United States Patent [19]
Keyes

[11] 3,933,589
[45] Jan. 20, 1976

[54] CHEMICAL IMMOBILIZATION OF ENZYMES

[75] Inventor: Melvin H. Keyes, Sylvania, Ohio

[73] Assignee: Owens-Illinois, Inc., Toledo, Ohio

[22] Filed: Mar. 20, 1975

[21] Appl. No.: 560,308

[52] U.S. Cl............................ 195/68; 195/DIG. 11
[51] Int. Cl.² ......................................... C07G 7/02
[58] Field of Search................ 195/68, 63, DIG. 11

[56] References Cited
UNITED STATES PATENTS 3,883,394   5/1975   Savidge et al......................... 195/63

*Primary Examiner*—Lionel M. Shapiro
*Attorney, Agent, or Firm*—Howard G. Bruss, Jr.; E. J. Holler

[57] ABSTRACT

Disclosed is a method for chemically immobilizing enzymes on a support to form a biologically active composite having prolonged service life by using a preformed reaction solution of an alkane dihalide and an alkane diamine for the chemical immobilization.

19 Claims, No Drawings

CHEMICAL IMMOBILIZATION OF ENZYMES

Enzymes are biologically active proteins which catalyze specific reactions. Enzymes have been used for a wide variety of industrial and research applications, particularly in fermentation, pharmaceuticals, medical research, and food processing. They are highly specific in their biological activity and generally do not generate significant quantities of undesirable by-products.

Recently attempts have been made to chemically or physically immobilize enzymes on various supports in the interest of efficient recovery and reuse. In the past, enzymes have been immobilized by attachment to inorganic supporting matrices by covalent coupling, adsorption, and ionic bonding. Covalent coupling of enzymes to water insoluble supports has been intensively investigated. Most of the supports have been organic polymers although recent reports have appeared where coupling agents have been used to attach enzymes to ceramic materials. For instance, U.S. Pat. No. 3,519,538 describes the use of silane coupling agents to attach enzymes to inorganic supports such as glass or alumina.

Adsorption of enzymes to water insoluble supports, whether organic or inorganic, has been the simplest insolubilization technique. It has been attractive because it requires merely exposing the enzyme in solution to the support material. The ease of adsorption, however, is offset by the corresponding ease of desorption. U.S. Pat. Nos. 3,556,945 and 3,850,751 disclose techniques for adsorption of enzymes to porous inorganic supports.

Another technique involves bonding the enzyme to the support in the presence of substrate and thus apparently blocking the active sites of the enzyme to avoid reaction of these sites with the support. Powdered glass and alumina are used for these applications in U.S. Pat. No. 3,666,627.

Further details on such prior art techniques can be found in the book entitled "Biochemical Aspects of Reactions on Solid Supports", edited by George R. Stark, Academic Press, New York, N.Y. (1971); the article entitled "Enzymes Immobilized on Inorganic Carriers" by H. H. Weetall appearing in Research/Development, December (1971); the article entitled "The Potential Applications of Molecular Inclusion to Beer Processing" by R. A. Messing appearing in the December 1971 issue of the Brewer's Digest; U.S. Pat. Nos. 3,512,987 and 3,167,485.

While these prior art techniques are suitable for many applications, the need exists for a simple, efficient, and economical method for chemically immobilizing enzymes to form an enzymatically active composite which retains a relatively high proportion of their initial activity even after conditions of prolonged storage and use.

In attaining the objects of this invention, one feature resides in immobilizing an enzyme on a support wherein an enzyme support and a chemical immobilizing agent are maintained in contact at a temperature and for a time sufficient to chemically immobilize the enzyme wherein the chemical immobilizing agent comprises a preformed reaction solution of an alkane dihalide and an alkane diamine.

As used herein the term "alkane dihalide" refers to an alkane having two halo groups such as bromo, iodo, chloro, or mixtures thereof in their molecular structure. The term "alkane diamine" refers to an alkane compound having two amino groups in its molecular structure. In the usual practice of the present invention, the alkane groups have 1 to 10 carbon atoms and preferably 1 to 6 carbon atoms for ease in forming the reaction solution. It has been observed that the solubility of the alkane dihalides in aqueous solutions have a tendency to decrease as the number of carbon atoms in the alkane group increases.

Such alkane diamines include branched and straight chain alkane diamines including diaminomethane, diaminoethane, diaminopropane, diaminobutane, diaminopentane, diaminodiaminoisooctane, diaminohexane, diaminoheptane, diaminooctane, diaminoisobutane, and diaminoisohexane. The position of the amino group on the alkane group has not been found to be critical to the practice of the present invention.

Suitable alkane dihalides include dibromo, diodo, and dichloro branched and straight chain alkane dihalides such as dibromomethane, dibromoethane, dibromopropane, diodopropane, dibromopentane, dichloroethane, dibromobutane, diiodopentane, diiodomethane, dichloromethane, and other dihalo alkanes having 1 to 10 carbon atoms. The position of the halides group on the alkane group has not been found to be critical to the practice of the present invention.

In the usual practice of the present invention, the alkane groups have 1 to 10 carbon atoms and preferably 1 to 6 carbon atoms for ease in forming the reaction solution. It has been observed that the solubility of the alkane dihalides in aqueous solution has a tendency to decrease as the number of carbon atoms in the alkane group increases.

Enzymes are complex polypeptides and have amino and carboxyl functionality in their molecular structure and may be classified under three general headings: hydrolytic enzymes, redox enzymes, and transferase enzymes. The first group, hydrolytic enzymes include proteolytic enzymes which hydrolyze proteins, e.g., papain, ficin, pepsin, trypsin, chymotrypsin, bromelin, keratinase, carbohydrases which hydrolyze carbohydrates, e.g., celluloase, amylase, maltase, pectinase, chitanase; esterases which hydrolyze esters, e.g., lipase, cholinesterase, lecithinase, alkaline and acid phosphateases; nucleases which hydrolyze nucleic acid, e.g., ribonuclease, desoxyribonuclease; and amidases which hydrolyze amines, e.g., arginase, asparaginase, glutaminase, histidase, and urease. The second group are redox enzymes that catalyze oxidation or reduction reactions. These include glucose oxidase, xanthine oxidase, catalase, peroxidase, lipoxidase, and cytochrome reductase. In the third group are transferase enzymes that transfer groups from one molecule to another. Examples of these are glutamicpyruvic transaminase, glutamic-oxalacetic transaminase, transmethylase, phosphopyruvic transphosphorylase. It should be noted that the enzyme can be used alone or in combination with other enzymes in the practice of the present invention.

The composition of the support is not particularly critical as long as it is inert, dimensionally stable, and provides sufficient surface area for retention of enzyme. The support can be porous, fluid-permeable membranes as in U.S. Pat. No. 3,839,175 or porous particulates as in U.S. Pat. No. 3,850,751. When porous supports are used, they should be sufficiently porous and sorptive enough to retain enough enzyme to form a biologically active composite. In the commercially significant embodiments of the present invention, the immobilized enzyme/support composite will exhibit at least about 0.001 International Units (I.U.) of activity per cubic centimeter of composite.

An International Unit of biological activity has been defined as the amount of active enzyme which converts substrate to product at the rate of one micromole per minute.

It has been found that porous matrix having a volume porosity in the range of 10 percent to 80 percent and preferably in the range of 15–50 percent are quite suitable for the present purposes. The pore size of the support is critical in that it should not be so small as to prevent immobilization of the enzyme thereon. Average pore size diameters of either fluid permeable membrane or porous particulates in the range of 0.01 micron to 10 microns are suitable for most applications with 0.01 to 2 being preferred for efficiency and economy.

The porous particulate support can be refractory ceramic oxide powders such as alumina powder, zirconia powder, magnesia powder, silica powder, thoria powder, glass powder, powdered clay, powdered talc and the like. The particle size of the porous particulates is not critical although a size range of −5 mesh to plus 400 mesh is practical. For efficiency and economy the size fraction of −20 to +100 mesh (U.S. Sieve) is usually employed.

Porous, inert, rigid, dimensionally stable refractory fluid permeable membrane supports can be prepared by compacting such refractory oxide powders to form a "green compact" of the desired configuration. The green compacts are then fired for a time and at a temperature sufficient for sintering to yield porous, inert, rigid, dimensionally stable, fluid permeable refractory support. The sintering should not be at a temperature or for a time which would cause collapsing or coalescence of the particles to form a non-porous body. A convenient indication of the degree of sintering is a comparison of the actual density of the fired compact as compared to the theoretical density of the oxide being fired. Of the many oxides which can be used for the present purposes, alumina is preferred for its chemical durability and ease of fabrication.

In forming the support from the powdered refractory oxide, the powdered particle size is selected to yield a sintered compact having a porosity and pore size in the range set forth above. The techniques for compaction and sintering of the porous supports are well-known in the art and form no part of the present invention. Suffice it to say that compacting pressures in the range of 1,000 p.s.i. to 10,000 p.s.i. and sintering temperatures in the range of 1,300° to 1,700°C are commercially expedient. Additional details on compacting and sintering of refractory oxides can be obtained from the book "Oxide Ceramics" by E. Ryshkewitch, published in 1960 by Academic Press, New York, N.Y.

The porous matrix can also be made of porous metal such as porous silver or porous stainless steel.

The porous matrix can be in any geometric shape such as rod cylinder discs, plates, bars, and blocks and the like.

Other suitable supports can be in the form of natural and synthetic fibers such as polypropylene, polyethylene, cotton or wool, nylon, rayon, polyester or acrylic fiber. The support can also be a blend of both natural and synthetic fibers or can be inorganic fibers made from carbon, asbestos, glass or similar fibrous ceramics, such as aluminum silicate. Fibrous forms of metals such as copper and stainless steel can also be used. Support fiber diameters can range from about 0.001 to about 0.25 inch. Such fibrous materials are quite useful in forming filter cartridges as in U.S. Pat. No. 3,828,934 for in-line filtration applications where filtration and treatment with immobilized enzymes are accomplished in one application. This is especially useful in the chill proofing of beer.

In the usual practice, the preformed reaction solution is formed by mixing the alkane dihalide and alkane diamine in an aqueous solution until the components are thoroughly dissolved to the limits of their solubility. In some instances an organic phase can be present in addition to the preformed reaction solution. This condition is usually not desired when the residual organic phase has a tendency to denature the enzyme or detract from its performance.

In some instance, a proportion of water miscible organic solvent (e.g., 0.1% to 90% by weight) such as alcohols (e.g. methanol, ethanol, or propanol) or ketones (e.g. acetone or methyl ethyl ketone) can be incorporated to enhance solubility of the alkane dihalide and alkane diamine in the aqueous solution. In some instances, organic solvents can be used in forming the reaction solution without the presence of water as long as such solvents so not denature the enzyme. The concentration of each of these two alkane components in the reaction solution is not particularly critical for the present invention and proportions in the range of 0.001% by weight to 5% by weight of each component are believed to be suitable for most applications with the solubility limit usually dictating the upper range of concentration.

As soon as the components are dissolved, the reaction solution is ready for use in immobilizing enzymes. Such dissolution readily takes place at temperatures from 20°C (i.e. room temperature) to the boiling point of the mixture in a time period of from a few seconds to an hour or longer. Temperatures in the range of about 20°C to about 50°C for a time ranging from about one minute to about one-half hour are convenient and practical.

The molar proportion of alkane diamine to alkane dihalide has not been observed to be critical in the practice of the present invention. Empirical observations have confirmed the molar ratio of alkane diamine to alkane dihalide over the range of 0.005:1 to 1000:1 provides satisfactory results with such ratio in the range of 0.1 to 20 being practical for many applications. The pH of the resulting preformed reaction solution is not particularly critical although a pH in the range of 2.5 to 11 is practical depending on enzymes used and pH obtained in the final solution. It is understood, of course, that the nature of the support or activity characteristics of the particular enzyme can require a higher or lower pH in some applications.

It is not presently understood whether or not there is a complete chemical reaction between the alkane dihalide and alkane diamine. It is known in the art that these components can react to form complex polyalkylene compounds as described in U.S. Pat. No. 2,696,504. It is not known that this reaction proceeds when practicing the present invention and the formation and isolation of such intermediate compounds is not part of the present invention. In this regard, the term "preformed reaction solution" is used to indicate that the alkane dihalide and alkane diamine are mixed to solution prior to contact with either the enzyme or support.

In carrying out the process of the present invention the enzyme, preformed reaction solution and support are brought into contact for time and temperature sufficient to chemically immobilize the enzyme in-situ on a support. This usually requires time periods ranging from a few minutes to several (e.g. 100) hours depending on the temperature, concentration, and other factors. The temperature is usually maintained below about 20°C or 30°C and usually about 0°C to 10°C to prevent denaturing the enzyme.

In accomplishing this contact the enzyme can be first deposited (e.g sorbed or impregnated) in the support and then contacted with the preformed reaction solution to chemically immobilize the enzyme. "Sorbed" is used to include adsorption and absorption. In another practice, the support can be contacted with the preformed reaction solution and then the enzyme is contacted therewith. In yet another practice the enzyme and the preformed reaction solution can be contacted prior to contact with the support. Of these, the first procedure is preferred for efficiency and economy in that the enzyme is first deposited on or impregnated into the support to achieve maximum "wetting" of the support with enzyme and the in-situ crosslinking "anchors" or bonds the enzyme into this position to assure high activity and prolonged retention of service life.

The immobilization techniques of the present invention are particularly useful in immobilizing glucose oxidase in the analysis of glucose according to U.S. patent application Ser. No. 477,922 filed June 10, 1974; and immobilizing urease in the analysis of urea according to U.S. patent application Ser. No, 427,322 filed Dec. 21, 1973; the immobilization of papain and other enzymes in the chill proofing of beer and amylases for hydrolysis of starch. For convenience of disclosure, all of the patents and references noted herein are incorporated by reference.

In the Examples that follow, all parts are parts by weight, all percentages are weight percentages, and all temperatures are in °C unless stated otherwise.

EXAMPLE 1

Part A—Immobilized Glucose Oxidase on Alumina Powder

One gram of particulate alumina is washed thoroughly with distilled water. The particulate alumina has a particle size in the range of −40 to +70 mesh (U.S. sieve screen) and an average pore size diameter of 0.1 to 0.2 microns.

Fifty mg of glucose oxidase (obtained from Worthington Biochemical Corporation having a reported activity of 140 International Units per milligram) is added to the wet particulate alumina in 40 ml of an aqueous solution which has been buffered to pH 5.5 with standard buffer comprising a mixture of potassium dihydrogen phosphate and disodium hydrogen phosphate. The resulting mixture is stirred gently for one-half hour at 6°–8°C to sorb enzyme.

To this mixture is added a preformed crosslinking reaction solution formed by mixing 20 ml methanol; 10 ml distilled water; 0.15 ml concentrated hydrochloric acid; 0.08 ml diaminopropane; and 0.02 ml dibromoethane at room temperature for about 15 minutes to form a solution. This corresponds to about a 4 to 1 mole ratio of diaminopropane to dibromoethane. The combined alumina, glucose oxidase and crosslinking reaction mixture is stirred gently with a magnetic stirrer at 6° to 8°C overnight to immobilize the glucose oxidase on the alunina. The resulting immobilized glucose oxidase/alumina composite is washed with about 2 liters of distilled water and stored in distilled water.

Part B—Assay of Immobilized Glucose Oxidase/Alumina Composite

The catalytic activity of the immobilized glucose oxidase/alumina composite of Part A is calculated from the measure rate of oxidation of β-D-glucose to gluconic acid by para-benzoquinone in the presence of the glucose oxidase/alumina composite. The reaction is represented by:

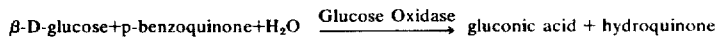

$$\beta\text{-D-glucose} + \text{p-benzoquinone} + H_2O \xrightarrow{\text{Glucose Oxidase}} \text{gluconic acid} + \text{hydroquinone}$$

The reaction is followed by measuring potentiometrically the change in concentration of hydroquinone with time. A platinum detector electrode (Beckman model 39273) is used with a double junction calomel-silver/-silver chloride reference electrode (Orion model 90-20-00). Standard solutions for calibrating the electrode system are prepared from hydroquinone with at least a 100 molar excess of p-benzoquinone also present in the aqueous solutions or in buffered solution pH = 5.5. The concentration of p-benzoquinone is 0.01M. A calibration graph is drawn by plotting hydroquinone concentration against millivolt readings from the potentiometer.

The reaction medium in which the oxidation of glucose takes place is an aqueous solution which is 0.1 molar in dextrose and 0.01 molar in phosphate buffer at pH 5.5. It is stirred overnight to assure that equilibrium has been reached between the α and β-D-glucose forms. Sufficient p-benzoquinone and hydroquinone is added to make the final solution $1.0 \times 10^{-2}M$ and $1.0 \times 10^{-4}M$ in these latter two components. A quantity of the glucose oxidase/alumina composite is added to a given volume of the reaction medium and the change in the potential of the electrode immersed in the solution is followed with time using the electrode system described above. From the millivolt readings the corresponding concentration of hydroquinone is determined from the calibration graph and a plot is made of test solution cencentration versus time. The initial slope of this curve represents the rate of oxidation of β-D-glucose catalyzed by the immobilized enzyme. The activity is calculated from the relationship:

$$\text{Activity} = \frac{\text{Rate of oxidation}}{\text{Volume of alumina}}$$

Using this assay procedure the glucose oxidase/alumina composite of Part A is found to have an activity of $1.0 \times 10^3$ International Units of glucose oxidase per cm³ of glucose oxidase/alumina composite. Ten days later, after being stored in distilled water at 4°C, the activity is $8.3 \times 10^2$ International Units of glucose oxidase per cm³ of glucose oxidase/alumina composite.

An International Unit of biological activity has been defined as the amount of active enzyme which converts substrate to product at the rate of one micromole per minute.

The glucose oxidase/alumina composite is used in the analysis of glucose as in Example 1 of application Ser. No. 477,922 filed June 10, 1974 and good results are obtained from the standpoint of accuracy, precision, and service life.

Similar results are obtained when diaminobutane and methylene diiodide are substituted for diaminopropane and dibromoethane on a molar basis in the foregoing procedures.

Similar results are also obtained when diaminopentane and dibromopropane are substituted for diaminopropane and dibromoethane on a molar basis in the foregoing procedures.

EXAMPLE 2

Preparation of Immobilized Glucose Oxidase

Five grams of particulate alumina having a particle size in the range of −60 to +70 mesh (U.S. sieve screen) and an average pore diameter of 0.1 to 0.2 microns is heated at 1150°C for 2 hours. After cooling, the particulate alumina is soaked in 1.0N HCl overnight. It is then washed with distilled water and placed in a beaker with 50 ml of 0.001 phosphate buffer (pH 6.0) for one-half hour before adding 25 ml of glucose oxidase solution. The glucose oxidase (Asperilligus niger) is obtained from Pierce Chemical Company in a buffered solution (pH 4.0) and has a reported activity of 1000 International Units/ml. The resulting glucose oxidase/alumina mixture is stirred gently for one-half hour at 3°–8°C.

A crosslinking reaction solution is prepared by mixing 20 ml methanol, 0.01 ml diaminopropane, 0.15 ml concentrated HCl, 0.03 ml dibromoethane and 10 ml water at room temperature for about 15 minutes. The mole ratio of diaminopropane to dibromethane is about 0.3 to 1.0. This preformed reaction solution is added at a rate of 0.15 to 0.20 ml/min. to the glucose oxidase/alumina mixture while stirring gently with a magnetic stirrer and maintaining the temperature at 3° to 8°C for 16–20 hours. The resulting immobilized glucose oxidase/alumina composite is washed with 2 liters of distilled water and stored in distilled water until assayed.

The assay procedure is the same as that described in Example 1. The activity of the sample is $2.3 \times 10^{+3}$ International Units/ml immobilized glucose/alumina composite.

The glucose oxidase/alumina composite is used in the analysis of glucose as in Example 3 of application Ser. No. 477,922 filed June 10, 1974 and good results are obtained from the standpoint of accuracy, precision, and service life.

EXAMPLE 3

Part A—(Sorbed Urease)

Urease (jack-bean meal sold by Worthington Biochemical Corporation having an initial activity of 63 I.U./mg) is immobilized on a particulate porous alumina support by mixing 100 mg urease and 1.0 g of particulate alumina in 200 ml of 0.01M tris (hydroxymethyl) aminomethane (adjusted and maintained at pH 8.2 with dilute HCl or dilute NaOH) at 40°C and stirring for 1 hour. The particulate alumina has a particle size in range of from −50 to +100 mesh (U.S. sieve screen) and an average pore size diameter of about 0.1 to 0.2 microns. The immobilized urease/alumina reaction product is allowed to stand overnight at 0°.

The immobilized urease reaction product is then vacuum filtered on a sintered glass funnel and washed first with 500 ml of 0.5 M NaCl, followed by washing with 1 to 2 liters of distilled water. The washed immobilized urease reaction product is stored in 10–20 ml of 0.01 M tris (hydroxymethyl) aminomethane buffer until ready to use. The initial activity of the immobilized urease/alumina product is assayed to be $1.5 \times 10^3$ I.U./cm$^3$ by the method described in Ser. No. 427,322 filed Dec. 21, 1973. After storage for 11 days the product is placed in a continuous flow stream buffer for one day and the activity is assayed at 61 I.U./cm$^3$.

Part B—(Crosslinked with Alkane Dihalides)

A solution of 1,2-dibromoethane is prepared by diluting 0.25 ml of 1,2-dibromoethane in 20 ml of methanol. This dibromoethane solution is added to 200 ml of a 0.01 M tris (hydroxymethyl) aminomethane at pH 8.2 buffered solution. The pH of the resulting solution is adjusted to and maintained at 8.2 by the dropwise addition of dilute HCl or dilute NaOH as required.

One hundred mg of urease and 1.0 g porous alumina powder (the same alumina powder used in Part A) are slowly added to the buffered dibromoethane solution with stirring while keeping the temperature at 40°C. This reaction mixture is stirred for 1 hour at 40°C and allowed to stand overnight at 0°. After filtering and washing the immobilized urease/alumina composite is assayed and determined to have an initial activity of $6.2 \times 10^2$ I.U./cm$^3$. After storage for 11 days the product is placed in a flow stream for one day under conditions similar to Part A and the activity is assayed to be $4.7 \times 10^2$ I.U./cm$^3$.

Part C—(Crosslinked with Alkane Diamine)

The procedures of Part B are repeated except that 0.75 ml of 1,3-diaminopropane is used in place of the dibromoethane solution from Part B. The initial activity of the immobilized urease/alumina product is assayed to be $1.4 \times 10^3$ I.U./cm$^3$ by the method described in Ser. No. 427,322 filed Dec. 21, 1973. After storage for 11 days the product is placed in a flow stream buffer for 1 day and the activity is assayed at $4.7 \times 10^2$ I.U./cm$^3$.

Part D—(Crosslinked with Preformed Solution of Alkane Diamine and Alkane Dihalides)

The procedures of Part B are repeated except that a preformed reaction solution of 0.02 ml of 1,2-dibromoethane and 0.08 ml of 1,3-diaminopropane in 20 ml of methanol is used in place of the dibromoethane solution. Also, 5 gm of alumina and 250 mg of urease purchased from Worthington Biochemical Corporation having an activity of approximately 160 I.U./mg are used. Therefore, 50 mg of urease is present per gram of alumina compared with 100 mg of the less active urease per gm of alumina in Parts A, B, and C. However, it should be noted that the quantity of active urease per gm of alumina is nearly the same in all four parts.

All solutions are prepared at room temperature while the immobilization reaction is allowed to proceed overnight at 0°–5°C. The initial activity of this immobilized urease/alumina composite is $1.2 \times 10^3$ I.U./ml. One week later, the activity is measured as 962 I.U./ml alumina.

After this measurement in activity, a column using this material is prepared and used for urea analysis as in Ser. No. 427,322 filed Dec. 21, 1973. After use in this nearly continuous flow system for 22 days, no loss in activity could be detected. Seven hundred and seventy-five samples of which 452 are serum samples are analyzed with good results from the standpoint of precision and accuracy during this three week period. In contrast to the stability of the immobilized urease prepared according to the procedure in Part D, the activity of samples A, B, and C are 28, 93, and 4 respectively when exposed to similar conditions.

EXAMPLE 4

In this experiment non-porous alumina is used as the support material. The alumina is a non-porous minus 100 mesh powder which has been acid washed.

A 400 mg sample of urease having an activity of 162 I.U./mg is dissolved in 200 ml water and centrifuged to give a clear supernatant solution. This solution is added to about 3 g of the above alumina and the resulting mixture is stirred for 12 hours while keeping the temperature at about 2°C.

A chemical immobilization reagent mixture is prepared by combining 0.1 ml of 1,2-dibromoethane, 0.1 ml of 1,3-diaminopropane, 20 ml methanol and 30 ml distilled water and adjusting the resulting mixture to a pH of 7.25 with hydrochloric acid. This corresponds to a one-to-one mole ratio of diaminopropane to dibromoethane. This reagent mixture is added to the urease/alumina mixture and the resulting combination is maintained at about 2°C for an additional 12 hours. The resulting urease/alumina composite is washed first with 0.4 M NaCl then with 0.001 M beta-mercaptoethanol, and finally with distilled water.

Assay of the washed urease/alumina composite product gives an activity of 137 I.U./ml.

EXAMPLE 5

A 20 g sample of alumina like that of Example 1 having a particle size between minus 40 and plus 50 mesh, U.S. Standard Sieve, is washed thoroughly with 4 l of distilled water. This alumina is placed in a vacuum flask and 400 ml of $2 \times 10^{-3}$M tris-maleate buffer at pH 8.9 [tris (hydroxymethyl) aminomethane and maleic acid in one-to-one molar ratio with sufficient NaOH or HCl to adjust the pH] is added. A water aspirator vacuum is applied and the flask shaken periodically for one-half hour. This buffer solution is then decanted and discarded and a fresh 300 ml of the same buffer solution is added.

One gram of urease is dissolved in 120 ml of the tris-maleate buffer solution and centrifuged at 8000 g's of force for 20 minutes. The urease solution is added to the alumina buffer solution and the mixture is vigorously shaken for one-half hour at 0° to 6°C.

A crosslinking reaction solution is prepared by dissolving 0.08 ml of 1,2-dibromoethane and 0.32 ml of 1,3-diaminopropane in 80 ml of methanol and 40 ml of distilled water. This corresponds to about a 4 to 1 mole ratio of diaminopropane to dibromoethane. This reaction mixture is stirred for one-half hour and the pH is adjusted to about 8 with hydrochloric acid. The crosslinking reaction mixture is then slowly added to the urease/alumina composite mixture with mild agitation while maintaining the temperature at 0°–6°C. These conditions of temperature and agitation are maintained for about 15 hours.

At the end of this period, the urease/alumina composite is filtered and washed with 1–2 liters of a $2.0 \times 10^{-3}$M trismaleate buffer solution, pH 7.0, which is 1.0 M in NaCl and $5.0 \times 10^{-3}$M in EDTA. The freshly washed urease/alumina composite has an initial activity of $2.2 \times 10^{+2}$ I.U./ml.

The procedures just described are repeated in a series of fifteen experiments. In this series the mesh size of the alumina is varied over the range of about 40 mesh to about 100 mesh and urease having a range of enzymatic activity from 50 to 160 I.U./mg obtained from several different supply sources is employed. The initial activities of the resulting urease/alumina composites from these fifteen experiments varies from about 100 I.U./cm³ to about 750 I.U./cm³ with one low value, 52 I.U./ml, and one high value, 1370 I.U./ml.

In the above experiments it is sometimes desirable to heat the alumina to about 1050°C to 1100°C for a few hours to make the alumina more chemically durable. However, extensive heating at these temperatures can reduce porosity and can change the average pore size.

EXAMPLE 6

This example illustates in a very practical way the effectiveness of the crosslinking method described in previous examples and the stability it provides to the urease/alumina composite.

A portion of the urease/alumina composite prepared as in Example 3 Part D which has an initial activity of 1370 I.U./cm³ is packed in a tube to form a bed. The column is a 75 mm ID borosilicate glass tube with an inside diameter of 2.8 mm and an outside diameter of 6 mm. A 400 mesh nylon screen is attached to one end of the column to retain the enzyme components.

This column is incorporated into and uses the urea analysis apparatus described in FIG. 1 of application Ser. No. 427,322 filed Dec. 21, 1973. A buffered diluent of 0.01 M tris (hydroxymethyl) aminomethane which is $10^{-3}$M in disodium ethylenediaminetetraacetic acid containing 0.09 M NaCl; $10^{-5}$M NH$_4$Cl is pumped through the system at a rate of 1.3 ml/min. The base stream consists of a 0.03 N sodium hydroxide solution also flowing at 1.3 ml/min. Multiple 20 microliter samples of urea standard solutions, 14 and 70 mg urea/100 ml, are injected into the buffer stream at the top of the enzyme column. The electrode response is recorded and the electronic detector is calibrated.

Over the course of about 3 weeks a total of 1215 samples are injected into this column, 700 were serum samples and 515 were aqueous urea samples. The column is always at room temperature during this period. The effectiveness of the crosslinking in the urease/alumina product is shown by the fact that at the end of this series of experiments a 10 microliter sample from a 100 mg urea/100 ml standard solution is injected into the column and a 100 mg urea/ 100 ml reading within error is recorded by the detector. Thus, even after this prolonged use the activity of the column material is still sufficient to completely hydrolyze the urea in this sample.

Three urease/alumina composites which had been prepared in a manner similar to that described above in Example 5 (except that the alumina has a pore size distribution in the range of 0.002 to 0.5 microns) are assayed and then used to prepare columns for use in urea analysis as in Ser. No. 427,322 filed Dec. 21, 1973. Multiple samples of aqueous urea solutions (known concentrations) and serum are injected in the top of the columns over a time period of approximately 1 to 2 weeks. The column is maintained at room temperature in a buffer of 0.01M tris (hydroxymethyl) aminomethane, pH 7.0, which is about 1 × $10^{-3}$M in disodium salt of ethylenediaminetetraacetic acid when not in actual use.

The effectiveness of the enzyme composites are determined by establishing the maximum concentration of urea that can be passed through the column with 100% conversion. The results are shown in the following table.

| Sample | Initial Activity of Enzyme Composite | No. of Samples 20µl each | Elapsed time for column use | Urea concentration for 100% hydrolysis |
|---|---|---|---|---|
| A | 506 I.U./cc | 392 aqueous urea 180 serum | 12 days | about 120 mg urea / 100 ml |
| B | 309 | 363 aqueous urea 482 serum | 12 days | about 90 mg urea / 100 ml |
| C | 717 | 300 serum | 6 days | about 140 mg urea / 100 ml |

EXAMPLE 7

This example describes a series of experiments which illustrate the effect of varying molar ratios of diaminopropane and dibromoethane in the reagent mixture used to immobilize glucose oxidase on alumina. The experiments are done in an essentially identical manner. Thus, one gram of alumina, having a particle size of −60 to +70 mesh and an average pore diameter of 0.14 microns, is deareated by placing it in a flask with 25 – 30 ml of a 1.0 N HCl solution and applying a water aspirator vacuum to the flask for ½ hour. The HCl is decanted from the alumina and about 20 to 30 ml of distilled deionized water is used to transfer the alumina powder to a 50 ml beaker.

About 25 mg of glucose oxidase is dissolved in 25 ml of tris (hydroxymethyl) aminomethane buffer adjusted to pH 7.0 with HCl. This enzyme solution is added to the beaker containing the alumina and the resulting mixture is stirred gently for one half hour at room temperature.

A preformed reaction solution is prepared (with one exception shown below) by combining 0.08 ml 1,3-diaminopropane, the desired amount of 1,2-dibromoethane (see Table 2), 10 ml methanol, 5 ml water, and 0.15 ml of concentrated HCl. This reagent mixture is added at one time to the enzyme/ alumina mixture above and the resulting mixture is stirred gently overnight at room temperature.

In one case, experiment 7A a two layer mixture forms when 8.27 ml dibromoethane, 0.08 ml diaminopropane, 10 ml of $H_2O$ and 10 ml methanol are combined to form the preformed reaction solution. Ten ml of the solution in approximately 20 ml organic layer is used. To this is added 0.15 ml of concentrated HCl and this mixture is then added to the enzyme/alumina sample as above, stirring overnight at room temperature. The significance of this experiment (7A) may be subject to further interpretation in that the reaction solution appears to be present in the organic phase. It is clear from the data in Table 2, however, that optimum results are not obtained.

In some of the other experiments small amounts of an organic phase are also observed in addition to the preformed reaction solution in the aqueous mixture, apparently due to the solubility limitations of the dibromoethane. However, all of the material is transferred to the enzyme/alumina mixture and no deleterious effects could be associated with the presence of this organic phase.

In each experiment the enzyme/alumina composite is washed with 1–2 liters of deionized water and stored in 5 ml distilled deionized water at 0°–5°C until assayed.

The activities of the immobilized enzyme/alumina composites are measured as described in Part B of Example 1. The following table shows the effect of changing the diamine to dihalide ratio on the initial activity of the composite and, more importantly, the activity retained after two months in deionized distilled water.

| Experiment No. | Mole ratio Diaminopropane: Dibromoethane | Initial Activity of Composite × $10^{-2}$ | Activity after 2 months | Activity Retained |
|---|---|---|---|---|
| 7A | 0.01 | 2.6 I.U./ml | 23 I.U./ml | 9% |
| 7B | 0.1 | 1.4 | 56 | 41 |
| 7C | 1 | 1.6 | 36 | 22 |
| 7D | 10 | 1.1 | 26 | 23 |
| 7E | 100 | 1.3 | 43 | 34 |
| 7F | 1000 | 1.7 | 33 | 19 |

EXAMPLE 8

The support material is a polyester fiber obtained from Commercial Filters Corporation as Standard Honeycomb wound filter cartridge. The fiber is wound on a hollow, cylindrical, plastic core to form the filter cartridge. The cartridge is approximately 10 inches long with an inner diameter of 1.0 inch and an outer diameter of 2.5 inches. The thickness of the fiber wall is, therefore, approximately 0.75 inches. This filter is designed to remove 95% of particles having 5 microns or more from a fluid stream.

Filter tubes of this type are widely used in the chemical processing industry. Perry's Chemical Engineer's Handbook (Fifth Ed., Chapter 19, p. 83–5) describes filtration systems incorporating such filter tubes.

Papain is obtained from Worthington Biochemical Corporation which is observed to exhibit an activity of 2.9 I.U. per milligram toward the substrate casein.

The filter tube is washed in an aqueous solution of detergent. The tube is suspended in a two liter graduated cylinder and the detergent solution stirred with a magnetic stirrer for about 15–18 hours (overnight). Rinsing is accomplished by pouring off the detergent solution, adding about one liter of distilled water, and stirring for 20 – 30 minutes. This process is repeated with six more portions of distilled water.

In a similar manner, the filter tube is subsequently washed with 800 ml of 3M sodium chloride for 1 hour and rinsed three times with distilled water. Finally the filter tube is washed twice with a solution of 0.002M lactate buffer, pH 3.5, containing 0.01M zinc sulfate.

This lactate-zinc sulate buffer solution is prepared by first dissolving 2.12g of an 85 percent solution of lactic acid in 500 ml of distilled water and adjusting the pH to 3.5 with 0.1N sodium hydroxide. This solution is then further diluted to give a total volume of one liter. A 100 ml aliquot of the lactate solution is mixed with 100 ml of a 0.1 M zinc sulfate solution and this mixture diluted to one liter to provide the final lactate-zinc sulfate buffer solution.

The filter tube is suspended in the cylinder and 800 ml of fresh buffer solution is added. After cooling to about 5°C a 500 mg quantity of papain is added in small increments while stirring continuously. Stirring is continued for 15 minutes at this temperature.

An enzyme immobilization reaction solution is prepared by dissolving 0.01 ml of 1,3-diaminopropane and 1.8 ml of 1,2-dibromoethane in a solvent composed of 40 ml water and 160 ml spectral grade methanol. The mole ratio of diaminopropane to dibromoethane is 0.01 to 1.0. The pH is adjusted to 4.0 ± 0.5 with concentrated hydrochloric acid.

The enzyme-filter tube-buffer system above is cooled sufficiently to maintain the temperature of the buffer in the range of 0° to 5°C and stirred with a magnetic stirrer. The enzyme chemical immobilization reagent solution, at room temperature, is then added at a rate of 1 milliliter per minute. Stirring is continued for 15 – 18 hours (overnight) at 0°–5°C. the pH is 3.6.

The filter tube is washed twice at room temperature using the technique previously described, with an 800 ml solution of 0.01 M tris-maleate buffer which is 0.001 M in zinc sulfate and 3.0 M in sodium chloride. The pH of the buffer is 6.0. The filter tube is stored in this solution at 0°–5°C until analyzed or used in substrate conversion reactions.

Assay Procedure

The filter tube is removed from the storage solution and washed for 15 minutes with a solution made up of 800 ml 0.05 M $K_2HPO_4$, 8.0 ml of 0.1 M dithiothreitol (DTT) and 8.0 ml of 0.1 M ethylenediaminetetraacetic acid (EDTA). The assay procedure is basically that described by Weissler and Garza in Am. Soc. Brewing Chemists, Proc., p. 225–38 (1965).

A casein substrate solution is prepared according to the reference method and to 800 ml of this solution is added 8.0 ml of 0.1 M DTT and 8.1 ml of 0.1 M EDTA. This solution is maintained at room temperature and the washed filter tube containing the immobilized papain is suspended in it. The solution is stirred with a magnetic stirrer. Five milliliter aliquots of the substrate solution, in contact with the filter tube, are extracted at 1, 5, 10, 20, 30 and 60 minute intervals. To each aliquot is added 3 ml of a 30% solution of trichloroacetic acid and 2 ml of water. The samples are heated at 40°C for 30 minutes and filtered through a 2 micron filter. The optical densities of the filtrates are measured at 277 nm and the concentration of the tyrosine-containing hydrolysis product of casein, is determined from a calibration graph. A plot of sample tyrosine concentration versus time provides a straight line the slope of which is related to the rate of hydrolysis of casein by the immobilized papain. The result is expressed in international units per filter, the international unit being defined here as equivalent micromoles of tyrosine produced per minute. For the filter tube described above the activity is 19.3 International Units.

EXAMPLE 9

The procedures and quantities of Example 8 are used except the pH of the lactate buffer is adjusted to 4.5 and the papain solution is stirred for ½ hour in the presence of the filter tube before adding the diaminopropane/dibromoethane reaction mixture. The initial activity of the immobilized enzyme filter tube composite is 38.5 International Units. After four days stored in buffer at 0°–5°C the activity is 18.6 I.U./filter.

EXAMPLE 10

The enzyme support material is a filter tube identical to that described in Example 8 except the fibers are made of Orlon, an acrylonitrile based polymer from E. I. duPont de Nemours and Company.

The filter tube is soaked in 3N HCl overnight to remove sizing and other surface treatments. The filter tube is then washed four times with distilled water and then suspended in a stirred solution of 3.0 M NaCl for 1 hour. It is then washed again with four portions of distilled water and finally two times with a lactate/zinc sulfate buffer of pH 4.5.

The filter tube is suspended in 800 ml of the buffer which is then cooled to 0°–5°C and 8.0 grams of Walterstein papain (0.055 I.U./mg) is added in small increments. The resulting mixture is stirred for ½ hour and a chemical immobilization reaction solution is added at the rate of 1.0 ml/min. while continually stirring and maintaining the temperature of the system at 0°–5°C. The reaction solution consists of 0.01 ml 1,3-diaminopropane, 1.8 ml 1,2-dibromoethane, 40 ml distilled water, and 160 ml spectral grade methanol. This corresponds to a mole ratio of diaminopropane to dibromoethane of 0.01 to 1.0. The reaction is allowed to proceed for 15 – 18 hours (overnight). The pH of the reaction solution after this time is 5.0.

The immobilized enzyme/filter tube composite is washed and assayed as described in Example 8. The initial activity is 38 International Units. After 30 days storage in buffer at 0°–5°C, it is 11.6 International Units.

EXAMPLE 11

The enzyme support material is a fiber wound filter tube having the configuration and dimensions of that described in Example 8 except that the fibers are made of Dynel, a copolymer of vinyl chloride and acrylonitrile produced by Union Carbide Corporation. The filter tube is soaked in 3 N HCl overnight to remove sizing and other surface treatments.

After washing twice with a lactate/zinc sulfate buffer (pH 4–5) as previously described in Example 8 the filter tube is suspended in this buffer solution, impregnated with enzyme, and a chemical immobilization reaction solution is added. The enzyme immobilization procedure and subsequent assay is performed as described in Example 9 except that the papain solution is stirred for 2 hours in contact with the filter tube before adding the immobilization reaction solution. The activity for the filter tube is 30.4 International Units. After 24 days the activity of the filter tube is 2.9 International Units. Twenty-one days later, 45 days from preparation, the activity is 5.7 International Units. The immobilized enzyme/filter tube composite is stored in buffer at 0°–5°C between analysis.

EXAMPLE 12

This example describes the immobilization of a purified papain in the absence of lactate buffer. A 20 g sample of Wallerstein Papain 90 is dispersed in 200 ml of a 0.01 M zinc sulfate solution, pH 4.5. This dispersion is centrifuged for ½ hour at 10,400 g's and the precipitate which forms is discarded. To the supernatant is slowly added 62.6 g of sodium chloride while stirring slowly at room temperature. After 2 hours the mixture is centrifuged for 20 minutes at 10,000 g's. The supernatant is discarded and the precipitated papain is dissolved in 800 ml of 0.01 M zinc sulfate adjusted to a pH of 4.5 with dilute hydrochloric acid.

The papain solution is cooled to 0°–5°C and a filter tube like that prepared in Example 11 is suspended in it while stirring for 45 minutes. The dibromoethane/diaminopropane reaction solution, the same as that in Example 10, is added to the papain/filter system at a rate of 1.0 ml/min. and stirring is continued overnight. The immobilized enzyme/ filter tube composite is washed and assayed as described in Example 8. The activity is 58.6 International Units. After 6 days storage it is reassayed and found to be 39 I.U.

EXAMPLE 13

A 50 g sample of Wallerstein Papain 400 is dispersed in 400 ml of a 0.01 M zinc sulfate solution pH 4.5. It is centrifuged for ½ hour at 16,300 g's and the precipitate which forms is discarded. To the supernatant is added slowly 125.2 g sodium chloride and the resulting mixture is left standing at room temperature for 2 hours. It is then centrifuged at 16,300 g's for 40 minutes, the supernatant is discarded and the papain precipitate dissolved in 800 ml of the above zinc sulfate solution.

A Dynel filter tube is soaked in HCl as in Example 11 and washed with a 0.01 M zinc sulfate solution, pH 4.5, for 1 hour. It is then suspended in the previously described papain solution cooled to 0°–5°C.

The pH is adjusted to 4.8 with 1 N sodium hydroxide. The papain solution is stirred for 45 minutes and a reaction solution is added at the rate of 1.0 ml/min. The reaction solution consists of 0.01 ml 1,3-diaminopropane, 1.8 ml 1,2-dibromoethane, 40 ml of 0.005 M lactic acid, and 160 ml of spectral grade methanol adjusted to pH 3.3 with HCl. The diaminopropane to dibromoethane mole ratio is 0.01 to 1.0. After about 15 – 18 hours (overnight) the immobilized enzyme/filter tube composite is washed for 25 minutes with 800 ml of a 0.01 M tris-maleate buffer solution which is 0.001 M in zinc sulfate and 1.0 M in sodium chloride, pH 6.0. It is then washed twice more for 15 – 30 minutes each in an identical, but sodium chloride-free buffer. It is stored in this buffer at 0°–5°C until assayed. When assayed according to the procedures of Example 8 the filter tube is found to have an activity of 109 International Units. After 1 month storage in the buffer the activity is 94 International Units.

EXAMPLE 14

The enzyme support material is a filter tube identical to that described in Example 8 except the fibers are Orlon. The filter tube is washed first with a detergent solution and then in 3 N HCl for 2 days, i.e. the filter tube is suspended in a stirred solution of HCl. After rinsing with several portions of distilled deionized water, the filter is allowed to stand for about 1½ hours in a 0.01 M zinc sulfate solution at 0°–5°C.

An enzyme solution is prepared by first recrystallizing 50 grams of Wallerstein Papain 400. This is done by combining the enzyme in 400 ml of 0.01 M zinc sulfate and centrifuging for ½ hour at 14,000 g's of force. To the supernatant is slowly added 125.2 g NaCl and the mixture is allowed to stand at room temperature for two hours before recentrifugation. The precipitate is dissolved in 800 ml of 0.01 M zinc sulfate adjusted with 3N HCl to pH 4.8, and the filter tube is immersed in it. The pH is readjusted to 4.8, if necessary, and the system is maintained in a cooling batch at 0°–5°C for 45 minutes.

An enzyme immobilization solution is prepared by adding to 160 ml of methanol, 3.9 ml dibromomethane, 40 ml of 0.005 M aqueous solution of lactic acid, 0.03 ml 1,3-diaminopropane and sufficient hydrochloric acid to adjust the pH to 3.2. The diaminopropane to dibromomethane molar ratio is 0.0064 to 1.0. This solution is added at the rate of 1.0 ml/min. to the filter tube-enzyme system just described. After addition of the reagent, stirring and cooling is continued overnight. The pH is found to be 4.5 the next day.

The filter tube is washed with 800 ml each of the following washing solutions: (1) 0.01 M tris-maleate buffer which is 0.001 molar in zinc sulfate and 1.0 molar in NaCl and, (2) two portions of 0.01 M tris-maleate buffer which is 0.001 M in zinc sulfate.

The filter tube is stored in 3 to 4 liters of a fresh solution having the same composition as the last wash. It is kept at 0°–5°C until assayed.

The filter tube is assayed as in Example 8 and found to have an activity of 51 International Units.

EXAMPLE 15

A 3 gram sample of −70 to +80 mesh porous alumina is fired at 1050°C for 45 minutes. Upon cooling, an aqueous slurry of the powder is prepared with distilled water and used to pack a column which is 30.5 cm long and 2.0 mm in diameter.

Urease, 400 mg, is combined with 200 ml of water and centrifuged to remove any suspended insoluble material. The clear supernatant, pH 5.6, is cooled to 2°C and eluted through the column by means of a peristalic pump while maintaining the system at a low temperature. The urease solution is eluted through the column at a rate of 0.9 ml/min.

Chemical immobilization of the sorbed urease is affected by the subsequent elution through the column of a preformed reaction solution consiting of 0.1 ml of 1,2-dibromoethane, 0.4 ml of 1,3-diaminopropane, 20 ml of methanol, 30 ml of water, and sufficient concentrated HCl to adjust the pH to 7.25. The diaminopropane to dibromoethane mole ratio is 4.0 to 1.0. This mixture is slowly eluted through the column over a 5 hour period at room temperature.

The column is finally washed, first with 40 ml of 0.5 M NaCl, then 10 ml of 0.001 M beta-mercaptoethanol, and finally 50 ml of water.

Initial assay of the column indicated an activity in excess of $1.0 \times 10^3$ I.U./cm$^3$ of immobilized enzyme composite. Two days later, after storage in distilled water, the column is re-assayed. It is washed with and assayed in the presence of, a solution which is 0.001 molar each in beta-mercaptoethanol, ethylenediaminetetraacetic acid, and sodium azide. The activity is still in excess of $1.0 \times 10^{+3}$ I.U./cm$^3$ of immobilized enzyme composite.

Having thus described the invention, what is claimed is:

1. In the process for immobilizing an enzyme on a support, wherein an enzyme, a support and a chemical immobilizing agent are maintained in contact at a temperature and for a time sufficient to chemically immobilize said enzyme, the improvement wherein said chemical immobilizing agent comprises a preformed reaction solution of an alkane diamine and alkane dihalide.

2. The process of claim 1 wherein the mole ratio of alkane diamine to alkane dihalide is in the range of about 0.005:1 to about 1000:1.

3. The process of claim 1 wherein said solution is an aqueous solution.

4. The process of claim 1 wherein said enzyme is deposited on said support prior to contact with said solution.

5. The process of claim 1 wherein said solution contains a water-miscible organic solvent.

6. The process of claim 1 wherein said support is a porous matrix formed by compacting and sintering a refractory oxide powder.

7. The process of claim 1 wherein said support is in the form of fibers.

8. The process of claim 1 wherein said alkane dihalide contains 1 to 10 carbon atoms.

9. The process of claim 1 wherein said alkane diamine contains 1 to 10 carbon atoms.

10. The process for chemically immobilizing an enzyme on a support comprising the steps of
    depositing said enzyme on said support to form an enzyme/support composite,
    contacting said composite with a preformed reaction solution of an alkane dihalide and an alkane diamine,
    maintaining said composite and said reaction solution in contact at a temperature and for a time sufficient to chemically immobilize said enzyme.

11. The process of claim 10 wherein said enzyme is glucose oxidase.

12. The process of claim 10 wherein said enzyme is urease.

13. The process of claim 10 wherein said enzyme is papain.

14. The process of claim 10 wherein said solution is an aqueous solution.

15. The process of claim 13 wherein said alkane dihalide and said alkane diamine each contain 1 to 6 carbon atoms.

16. The process of claim 1 wherein said support is a refractory ceramic oxide powder.

17. The process of claim 16 wherein the particle size of said powder is in the range of $-5$ mesh to $+400$ mesh.

18. The process of claim 17 wherein the particle size of the powder is in the range of about $-20$ mesh to about $+100$ mesh.

19. The process of claim 10 wherein said support is a refractory ceramic oxide powder.

* * * * *